(12) United States Patent
Park et al.

(10) Patent No.: US 12,741,101 B2
(45) Date of Patent: Sep. 22, 2026

(54) MEDICINE INJECTION TIP, HAND PIECE, AND SKIN TREATMENT DEVICE

(71) Applicant: JEISYS MEDICAL INC., Seoul (KR)

(72) Inventors: Jong Seung Park, Seoul (KR); Kyoung Ho An, Seoul (KR); Min Young Kim, Seoul (KR); Won Ju Yi, Seoul (KR); Dong Hwan Kang, Seoul (KR)

(73) Assignee: JEISYS MEDICAL INC., Seoul (KR)

( * ) Notice: Subject to any disclaimer, the term of this patent is extended or adjusted under 35 U.S.C. 154(b) by 1144 days.

(21) Appl. No.: 17/742,056

(22) Filed: May 11, 2022

(65) Prior Publication Data

US 2022/0370731 A1 Nov. 24, 2022

(30) Foreign Application Priority Data

May 20, 2021 (KR) ........................ 10-2021-0064789

(51) Int. Cl.
*A61M 5/32* (2006.01)
*A61B 18/00* (2006.01)
(Continued)

(52) U.S. Cl.
CPC ....... *A61M 5/3298* (2013.01); *A61B 18/1477* (2013.01); *A61M 5/2053* (2013.01); *A61B 2018/0047* (2013.01)

(58) Field of Classification Search
CPC .............. A61M 5/3298; A61M 5/2053; A61M 37/0015; A61M 2037/0023; A61M 2037/0046; A61M 2037/0061; A61M 2210/04; A61M 37/00; A61M 37/0092; A61M 2037/0007; A61M 5/3287;
(Continued)

(56) References Cited

U.S. PATENT DOCUMENTS 4,393,870 A * 7/1983 Wagner ................. A61M 5/425
604/115
2004/0024367 A1* 2/2004 Gilbert .................. A61M 5/326
604/198
(Continued)

FOREIGN PATENT DOCUMENTS

CN 112368046 A 2/2021
JP H0734746 A 2/1995
(Continued)

OTHER PUBLICATIONS

Korean Intellectual Property Office, Notice of Office Action, May 30, 2023.

(Continued)

*Primary Examiner* — Michael J Tsai
*Assistant Examiner* — Kathleen Paige Vokes

(57) ABSTRACT

A medicine injection tip includes: a cylinder; a shaft in the cylinder and movable closer to or spaced apart from skin; a needle unit between the shaft and the skin; and a locking unit between the shaft and the needle unit to lock or unlock the shaft as the shaft is moved. A hook recess may be provided in any one of the shaft and the locking unit, and a hook locked to or unlocked from the hook recess is provided in the other of the shaft and the locking unit. The medicine injection tip may be mounted on a hand piece, which may be part of a skin treatment device.

15 Claims, 10 Drawing Sheets

(51) Int. Cl.
*A61B 18/14* (2006.01)
*A61M 5/20* (2006.01)

(58) Field of Classification Search
CPC ............ A61M 5/2033; A61M 5/31576; A61M 2005/14256; A61M 2005/3231; A61B 18/1477; A61B 2018/0047; A61B 18/1402; A61B 2018/00196; A61B 2018/143; A61B 2018/00452; A61B 2017/2931; A61N 1/18; A61N 7/00; A61N 1/328; A61N 2005/0644
See application file for complete search history.

(56) References Cited

U.S. PATENT DOCUMENTS

2012/0116389 A1* 5/2012 Houser .......... A61B 17/320092 606/1
2013/0211330 A1* 8/2013 Pedersen et al. ..... A61M 5/326
2014/0094742 A1 4/2014 Won
2020/0093996 A1* 3/2020 An .......................... A61N 1/06

FOREIGN PATENT DOCUMENTS

KR 101153700 B1 6/2012
KR 10-2062219 B1 1/2020
KR 20200059610 A 5/2020
KR 102241500 B1 4/2021
WO WO 2018131623 A1 7/2018

OTHER PUBLICATIONS

Chinese Patent Office, First Office Action, Dec. 5, 2023.
Japanese Patent Office, Notice of Reasons for Refusal regarding JP Application No. 2022-082535, Apr. 28, 2023.

* cited by examiner

MEDICINE INJECTION TIP, HAND PIECE, AND SKIN TREATMENT DEVICE

CROSS-REFERENCE TO RELATED APPLICATIONS

A claim for priority under 35 U.S.C. § 119 is made to Korean Patent Application No. 10-2021-0064789 filed on May 20, 2021 in the Korean Intellectual Property Office, the entire contents of which are hereby incorporated by reference.

BACKGROUND

Embodiments of the inventive concept described herein relate to a medicine injection tip, a hand piece, and a skin treatment device.

Skin treatment devices for removing wrinkles, restoring elasticity of skin, and removing sebum are being developed.

Skin that has no wrinkles, is tight, thick, and dense, and has no elongations gives more youthful look and contributes to a charming appearance.

There are several types of skin treatment devices, such as a method for delivering ultrasonic waves to skin tissues (HIFU type), a method for delivering high-frequency waves to skin tissues (RF type), and a method for irradiating laser rays to skin tissues (optical type).

The device of a type, which delivers high-frequency waves to skin tissues, allows radio frequency (RF) needles to invade into skin (for example, a dermal layer) of a target point (for example, a face) by using a hand piece provided with one or more RF needles, and removes collagen and elastic fibers damaged in the skin and expedites new formation thereof by using heat generated by the high-frequency waves. Moreover, the skin treatment device may form a hole in skin by using a needle for skin care, such as pigmentation of the skin, acne spots, and wrinkles, and the medicine may be injected into the hole.

Furthermore, the medicine may be injected regardless of whether the high-frequency wave is delivered in a process of reproducing the skin by using the needle.

In this way, a device that injects medicine to the skin by using a needle is called a medicine injection tip.

An existing medicine injection tip includes a medicine chamber, a needle provided in the medicine chamber to be moved reciprocally, an actuator that inserts the needle into the skin by moving the needle in a direction, in which the needle becomes closer to the skin, and a spring that provides an elastic force for moving the needle inserted into the skin in a direction, in which the needle is spaced apart from the skin.

However, the existing medicine injection tip may not be moved or delayed in a direction, in which the needle is spaced apart from the skin, when an elastic force of a spring becomes lower or a life span thereof expires.

RELATED ART DOCUMENT

Patent Document (Patent document 1) Korean Patent No. 10-2062219 (Dec. 27, 2019)

SUMMARY

Embodiments of the inventive concept has been devised to obviate the above limitation. An aspect of the inventive concept is directed to providing a medicine injection tip that may smoothly insert and discharge a needle into and from skin, a hand piece, and a skin treatment device.

The aspects of the inventive concept are not limited to the above-mentioned ones, and the other un-mentioned aspects will become apparent to those skilled in the art from the following description.

According to an embodiment of the inventive concept, a medicine injection tip includes: a cylinder; a shaft provided in the cylinder and being moved in a direction, in which the shaft becomes closer to or spaced apart from skin; a needle unit disposed between the shaft and the skin; and a locking unit provided between the shaft and the needle unit and configured to lock or unlock the shaft as the shaft is moved, wherein a hook recess is provided in any one of the shaft and the locking unit, and a hook locked to or unlocked from the hook recess is provided in the other of the shaft and the locking unit.

In addition, the locking unit may include a locking bracket being coaxial with the shaft and connected to the needle unit, and a locking arm elastically supported by the locking bracket and being moved in a direction, in which the locking arm becomes closer to or spaced apart from the shaft, wherein the hook recess or the hook may be formed in the locking arm.

In addition, the medicine injection tip may further include a guide provided in the cylinder and configured to guide movement of the locking arm.

In addition, the guide may include an unlocking path unit configured such that the locking arm is moved while being spaced apart from the shaft and while the hook recess and the hook are unlocked from each other, and a locking path unit configured such that the locking arm is moved while being adhered to the shaft and while the hook recess and the hook are locked to each other.

In addition, the unlocking path unit may be stepped from the locking path unit and may have an inner diameter that is relatively larger than that of the locking path unit.

In addition, the guide may include a gradient path unit having a specific gradient between the unlocking path unit and the locking path unit.

In addition, the locking arm may further include: a first outer diameter unit protruding and extending from the locking bracket; a gradient unit having a specific gradient corresponding to the gradient path unit and protruding and extending from the first outer diameter unit; and a second outer diameter unit stepped from the first outer diameter unit, having an outer diameter that is larger than that of the first outer diameter unit, and protruding and extending from the gradient unit.

In addition, the medicine injection tip may further include a medicine supply unit that supplies a medicine to the skin, and the medicine supply unit may include a medicine supply passage provided in the cylinder, and configured to supply the medicine to a vicinity of the skin when a negative pressure is formed at the vicinity of the skin, into which a needle is inserted.

In addition, the medicine supply unit may further include a medicine storage unit accommodated in the cylinder and in which the medicine supplied to the medicine supply passage is stored.

In addition, the needle unit may include a plunger forming a first space and a second space in an interior of the cylinder, and a needle disposed in the first space and fixed to the plunger, and the plunger may include a channel connecting the first space and the second space.

In addition, the needle may form an invasion hole, through which the needle is inserted into and discharged from the skin, as the needle unit is moved, a negative pressure may be formed in the second space such that the medicine is suctioned from the medicine supply passage when the needle is inserted into the skin, and a positive pressure may be formed in the second space such that the medicine is injected into the invasion hole when the needle is discharged from the skin.

In addition, electric energy may be applied to the needle.

In addition, the electric energy applied to the needle may generate thermal energy in the skin.

The aforementioned the medicine injection tip may be mounted on a hand piece according to an embodiment of the inventive concept.

A skin treatment device according to an embodiment of the inventive step may include a medicine injection tip, and a hand piece, on which the medicine injection tip is mounted.

Detailed items of the other embodiments are included in the detailed description and the accompanying drawings.

DETAILED DESCRIPTION

Figure 1:
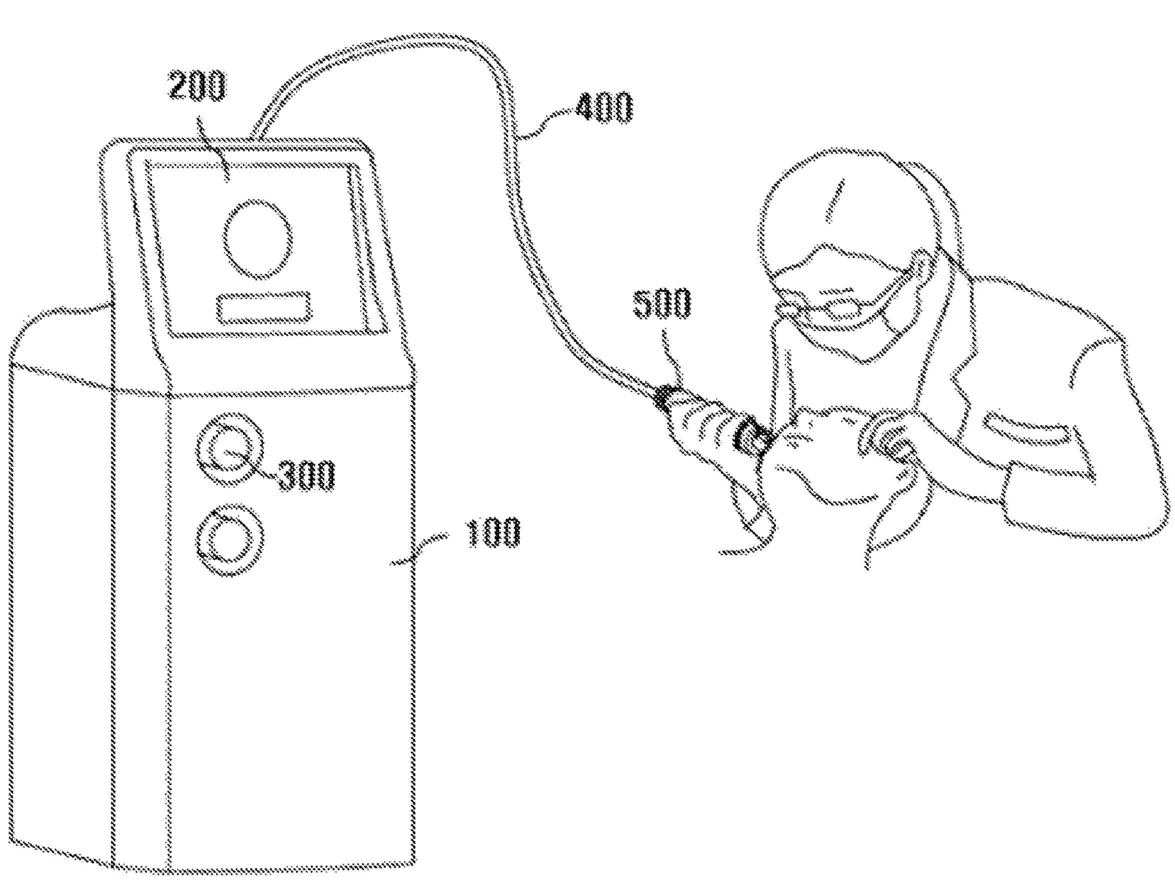
FIG. 1 is a perspective view illustrating a skin treatment device according to an embodiment of the inventive concept.

The above and other aspects, features, and advantages of the inventive concept will become apparent from the following description of the following embodiments given in conjunction with the accompanying drawings. However, the inventive concept is not limited by the embodiments disclosed herein but will be realized in various different forms, and the embodiments are provided only to make the disclosure of the inventive concept complete and fully inform the scope of the inventive concept to an ordinary person in the art, to which the inventive concept pertains, and the inventive concept will be defined by the scope of the claims.

The terms used herein are provided to describe the embodiments but not to limit the inventive concept. In the specification, the singular forms include plural forms unless particularly mentioned. The terms “comprises” and/or “comprising” used herein does not exclude presence or addition of one or more other elements, in addition to the aforementioned elements. Throughout the specification, the same reference numerals denote the same elements, and “and/or” includes the respective elements and all combinations of the elements. Although “first”, “second” and the like are used to describe various elements, the elements are not limited by the terms. The terms are used simply to distinguish one element from other elements. Accordingly, it is apparent that a first element mentioned in the following may be a second element without departing from the spirit of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

Hereinafter, exemplary embodiments of the inventive concept will be described in detail with reference to the accompanying drawings.

Figure 2:
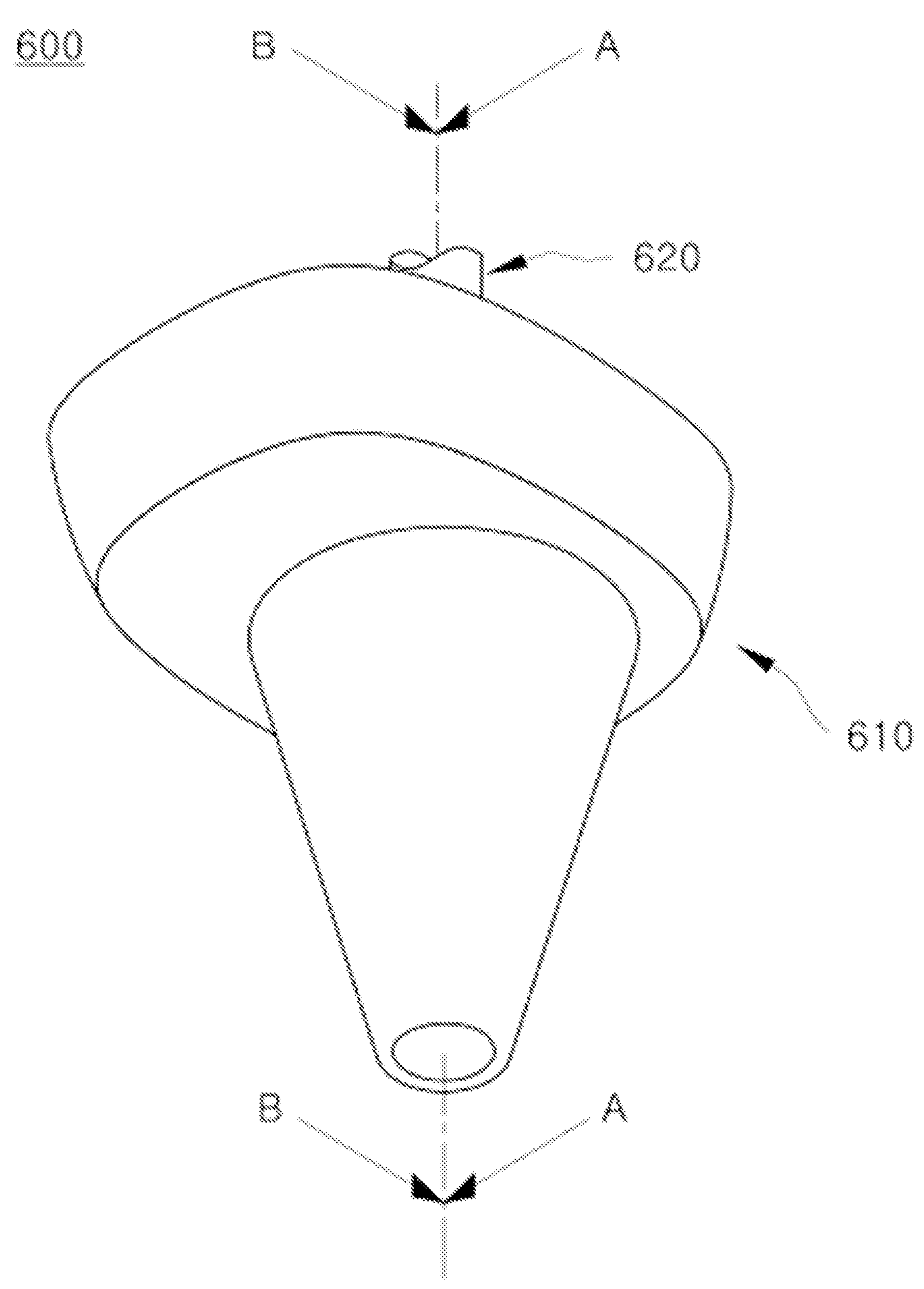
FIG. 2 is a perspective view illustrating a medicine injection tip according to an embodiment of the inventive concept.
Figure 3:
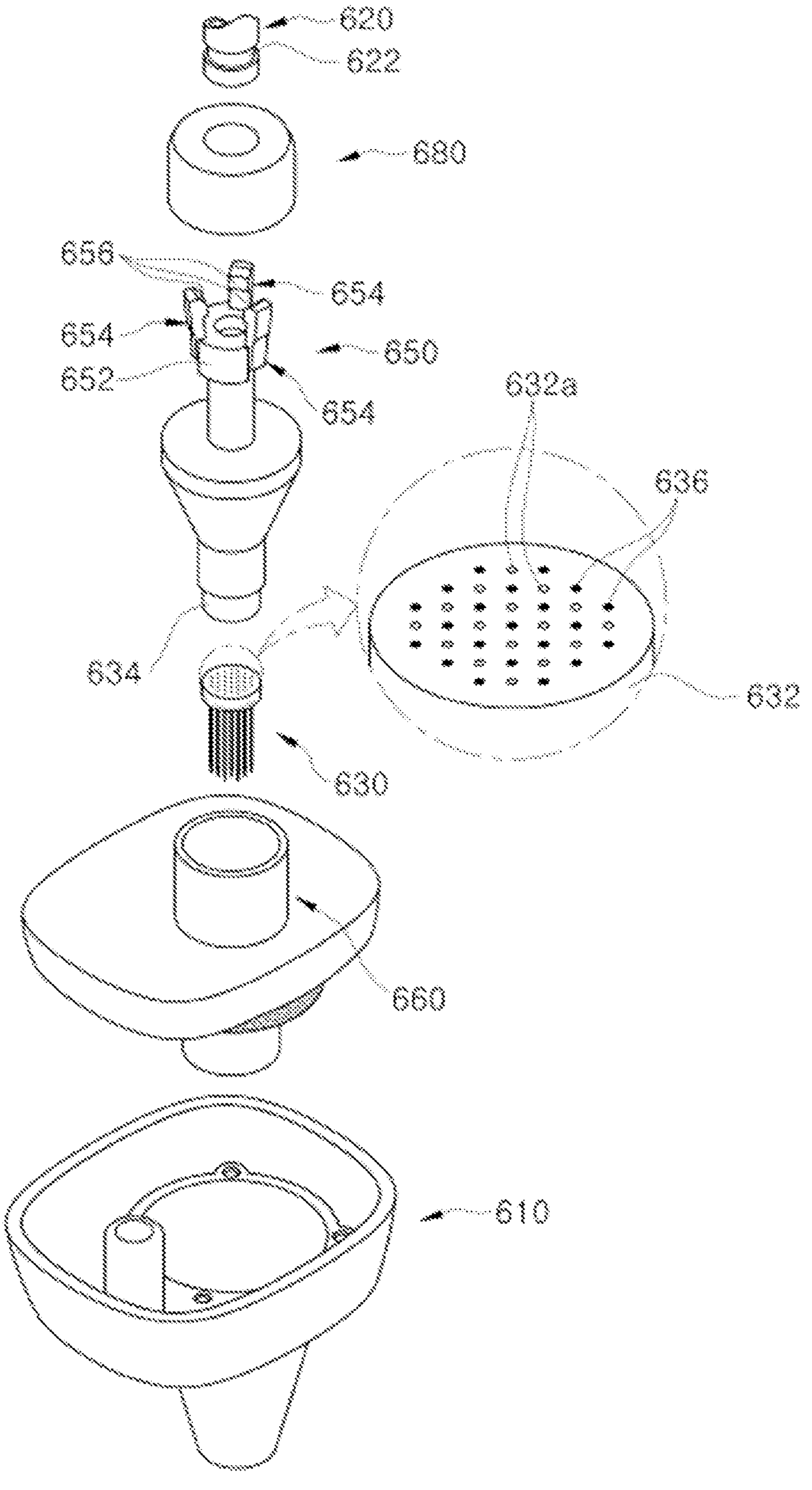
FIG. 3 is an exploded perspective view illustrating a medicine injection tip according to an embodiment of the inventive concept.
Figure 4:
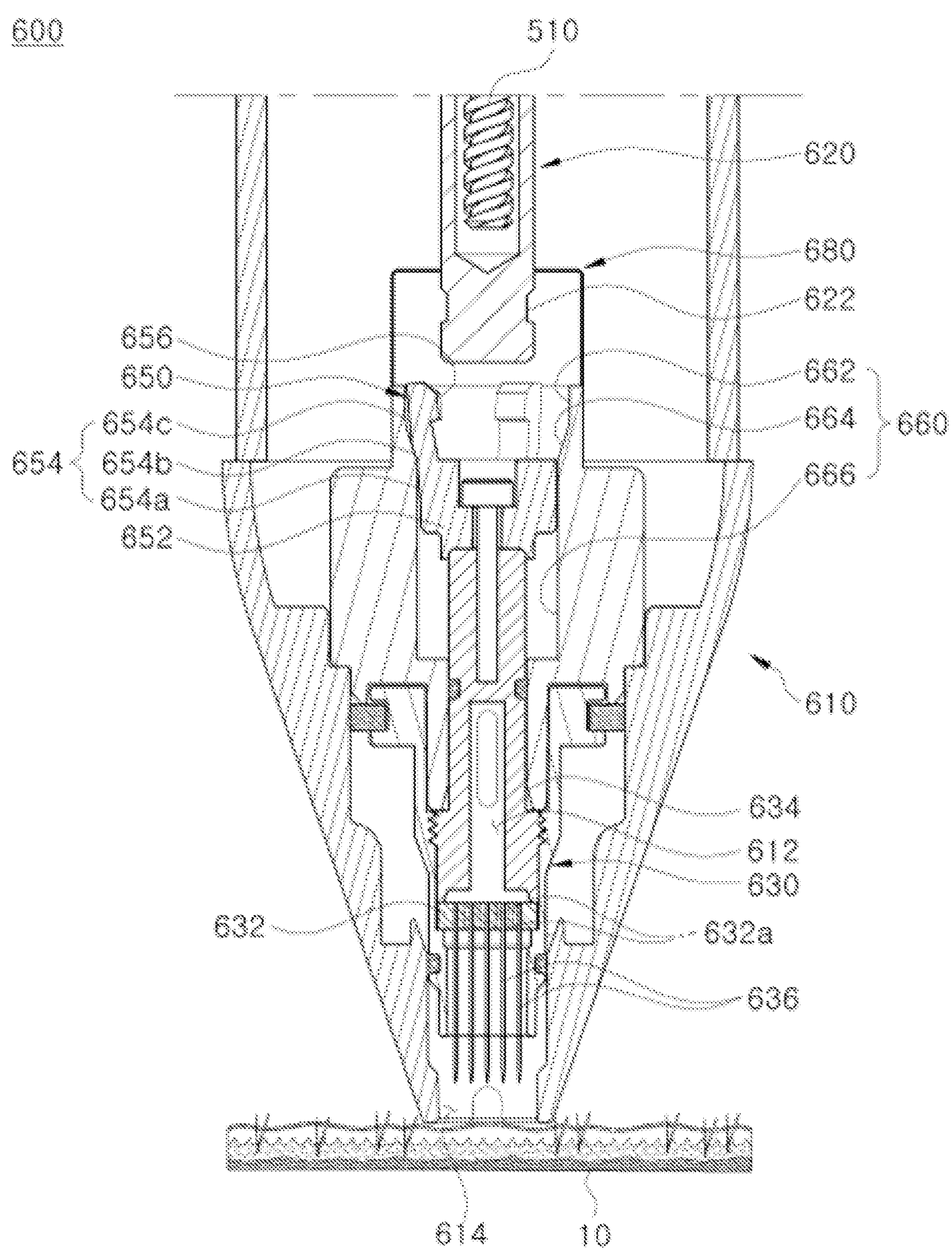
FIG. 4 is a cross-sectional view taken along line A-A' of FIG. 2.

FIG. 1 is a perspective view illustrating a skin treatment device according to an embodiment of the inventive concept. FIG. 2 is a perspective view illustrating a medicine injection tip according to the embodiment of the inventive concept. FIG. 3 is an exploded perspective view illustrating the medicine injection tip according to the embodiment of the inventive concept. FIG. 4 is a cross-sectional view taken along line A-A' of FIG. 2.

As illustrated in FIG. 1, the skin treatment device of the inventive concept may include a body 100, a display module 200, a manipulation module 300, an electronic control module (not illustrated), a cable 400, a hand piece 500, a medicine injection tip 600, a driving module (not illustrated), and a power source module (not illustrated).

The body 100 may be provided with the display module 200 and the manipulation module 300. The display module 200 may be manufactured in a form of a panel, and may visually provide various pieces of information to a surgical operator who conducts a skin 10 treatment operation. Accordingly, an output or an impedance of a high-frequency wave applied to a dermal layer at a current target point may be graphed and displayed on the display module 200. Furthermore, an operation mode that is currently performed by the skin treatment device of the inventive concept may be displayed on the display module 200. Furthermore, biometric information of skin 10 tissues and the like may also be displayed on the display module 200.

The manipulation module 300 may be provided on an outer surface of the body 100 in a form of a button. A surgical operator may switch on or off the skin treatment device through the manipulation module 300, may select an operation mode of the skin treatment device, and may change an output of the high-frequency wave applied to the target point.

Meanwhile, when the display module 200 is provided in a form of a touchscreen, at least a portion of the manipulation module 300 may be omitted. In this case, the skin treatment device may be manipulated by touching a menu that appears on a screen of the display module 200.

The electronic control module may be embedded in the body 100, and may electronically control constituent elements of the skin treatment device. To this end, the electronic control module may be electrically connected to the driving module and the power source module through the cable 400. That is, the electronic control module may apply the corresponding control signal to the driving module and the power source module according to a manipulation signal of a surgical operator.

As an example, a driving period of the driving module and the like may be controlled according to the control signal of the electronic control module. As a result, a reciprocation driving period of a needle unit 630 of the medicine injection tip 600 may be controlled.

Furthermore, an output of the power source module and the like may be controlled according to the control signal of the electronic control module. As a result, a wavelength, a direction, intensity, and the like of a current applied to one or more needles 636 of the needle unit 630 may be changed, and thus the output of the high-frequency wave applied to the target point and the like may be controlled.

Meanwhile, it is not necessary to essentially apply a high-frequency wave to the one or more needles 636 in the skin 10 treatment device of the inventive concept. That is, in consideration of a purpose, an effect, an economic efficiency, and the like of a treatment, electric energy may not be applied to the one or more needles 636. The electric energy, for example, may be a radio frequency (RF).

The cable 400 may perform a function of a conductive line that connects the electronic control module and the driving module or electrically connects the electronic control module and the power source module. To this end, the cable 400 may extend from the body 100 to one side, and may connect the body 100 and the hand piece 500. A plurality of electric wires may be embedded in the cable 400, and the plurality of electric wires may deliver an electric signal to the needles 636 through an electronic circuit such as a PCB.

The hand piece 500 is a part that is gripped by a surgical operator, and the surgical operator may change the target point (for example, a portion of a face) by moving the hand piece 500 while the hand piece 500 contacts the skin 10 of a subject. The hand piece 500 may be disposed in the cable 400, and may be located at a distal end of the cable 400 in an extension direction thereof.

The driving module and the power source module may be embedded in the hand piece 500. Accordingly, the cable 400 may electrically connect each of the driving module and the power source module embedded in the hand piece 500 to the electronic control module embedded in the body 100.

Here, the driving module may provide a driving force that moves a shaft 620 provided in a cylinder 610 of the medicine injection tip 600 in a direction, in which the shaft 620 becomes closer to or spaced apart from the skin 10.

The medicine injection tip 600 may be mounted at a distal end of the hand piece 500. In this case, the medicine injection tip 600 may be mounted at the distal end of the hand piece 500 to be exchangeable in a form of a cartridge.

As illustrated in FIGS. 2 to 4, the medicine injection tip 600 may include the cylinder 610, the shaft 620, the needle unit 630, a locking unit 650, and a guide 660.

The cylinder 610 may accommodate the shaft 620, the needle unit 630, and the locking unit 650 in an interior thereof, and may be coupled to the distal end of the hand piece to be separable.

A distal end of the cylinder 610 may be opened, and the distal end of the cylinder 610 may be disposed on a surface of the skin 10. As a result, an opening of the cylinder 610 may be closed by the surface of the skin 10.

The shaft 620 may be provided in the cylinder 610, and may be moved in a direction, in which the shaft 620 becomes closer to or spaced apart from the skin 10. The shaft 620 may be moved in the direction that becomes closer to or spaced apart from the skin 10 by the driving force of the driving module. Here, the direction, in which the shaft 620 becomes closer to or spaced apart from the skin 10, may be a downward or upward based on FIG. 4.

The shaft 620 may be disposed at a location that is spaced apart from the locking unit 650 at a specific interval in an initial stage. Accordingly, when the shaft 620 is moved in a direction, in which the shaft 620 becomes closer to the skin 10, the shaft 620 may be moved to a bottom dead point of the locking unit 650 after being locked to the locking unit 650 at a top dead point of the locking unit 650. Thereafter, when the shaft 620 is moved in a direction, in which the shaft 620 becomes spaced apart from the skin 10, the shaft 620 may be moved to an initial location after being unlocked from the locking unit 650 at a top dead point of the locking unit 650. Here, the top dead point of the locking unit 650 may be a location, to which the locking unit 650 may be moved maximally based on the direction, in which the locking unit 650 becomes farther from the skin 10, and the bottom dead point of the locking unit 650 may be a location, to which the locking unit 650 may be moved maximally based on the direction, in which the locking unit 650 becomes closer to the skin 10.

In an embodiment, the shaft 620 may have a form of a movable nut that is screw-coupled to a screw shaft 510 of the driving module. The shaft 620 may be moved along the screw shaft 510 when the screw shaft 510 is rotated by the driving force of the driving module.

The needle unit 630 may be inserted into or discharged from the skin 10 to form an invasion hole 11 or deliver electric energy to the skin 10. The needle unit 630 is disposed between the shaft 620 and the skin 10.

The needle unit 630 may be locked to the shaft 620 through the locking unit 650, and may be moved in a direction, in which the locking unit 650 becomes closer to or spaced apart from the skin 10 together with the shaft 620. Further, the needle unit 630 may be unlocked from the shaft 620 through the locking unit 650 to be stopped.

The needle unit 630 may include a plunger 632 and the needle 636.

The plunger 632 may be coupled to the locking unit 650, and may form a first space 612 and a second space 614 in an interior of the cylinder 610. Here, the first space 612 may be formed between the plunger 632 and the shaft 620 in the interior of the cylinder 610, or may be formed in an interior of a connecting rod 634. The second space 614 may be formed between the plunger 632 and the skin 10 in the interior of the cylinder 610. A channel **632*a* that connects the first space 612 and the second space 614 may be formed in the plunger 632**.

Meanwhile, the plunger 632 may be coupled to the locking unit 650 through the connecting rod 634, and the connecting rod 634 may be disposed in the second space 614 to connect the plunger 632 and the locking unit 650. However, the connecting rod 634 may be selectively provided.

The needle 636 may be disposed in the first space 612 to be fixed to the plunger 632. One or more needles 636 may be provided.

The needle 636 may be inserted into the skin 10 in contact with the distal end of the cylinder 610 while being moved in a direction, in which the needle 636 becomes closer to the skin 10 together with the plunger 632. Thereafter, the needle 636 may be discharged from the skin 10 while being moved in a direction, in which the needle 636 becomes spaced apart from the skin 10 together with the plunger 632. Thereafter, the invasion hole 11 may be formed in the skin 10 due to the insertion and discharge of the needle 636.

Electric energy may be applied to the needle 636, and the electric energy applied to the needle 636 may generate thermal energy in the skin 10. Here, the electric energy applied to the needle 636 may be applied to various frequency wavelength bands and ultrasonic waves, in addition of bands of high-frequency waves. Moreover, as described above, electric energy or ultrasonic wave may not be applied to the needle 636. When the electric energy is applied to the needle 636, the needle 636 may receive electric power from the power source module.

The needle 636 may be an electrode unit of a bipolar type, in which a plurality of electrodes have two polarities such that a high frequency is generated between adjacent electrodes, or may be an electrode unit of a mono-polar type, in which all of a plurality of electrodes have the same polarity. Meanwhile, when the needle 636 is of a mono-polar type, a ground electrode module (not illustrated) for returning the high-frequency wave generated in the needle 636 may be additionally provided.

As the plunger 632 is moved, the invasion hole 11, through which the needle 636 is inserted into and discharged from the skin 10 may be formed, and a negative pressure may be formed in the second space 614 and the medicine may be suctioned from a medicine supply passage (not illustrated) when the needle 636 is inserted into the skin 10 and a positive pressure may be formed in the second space 614 and the medicine may be injected into the invasion hole 11 when the needle 636 is discharged from the skin 10. The detailed description thereof will be made later.

Meanwhile, an elastic member (not illustrated) that elastically supports the needle unit 630 may be provided between the needle unit 630 and the distal end of the cylinder 610. The elastic member (not illustrated) may be a spring.

The locking unit 650 is provided between the shaft 620 and the needle unit 630 and is coupled to the needle unit 630 to lock or unlock the shaft 620 as the shaft 620 is moved. Here, because the shaft 620 is disposed at a location that is spaced apart from the locking unit 650 by a specific interval at an initial location, the locking unit 650 unlocks the shaft 620 while the shaft 620 is moved along a path between the initial location and the top dead point of the locking unit 650. Moreover, when the shaft 620 is moved in a section between the top dead point and the bottom dead point of the locking unit 650, the locking unit 650 may lock the shaft 620.

Meanwhile, a hook recess 622 may be provided in any one of the shaft 620 and the locking unit 650, and a hook 656 that is locked to or unlocked from the hook recess 622 may be provided in the other of the shaft 620 and the locking unit 650. The hook recess 622 and the hook 656 function to substantially lock or unlock the locking unit 650 and the shaft 620, and a description thereof will be made later.

The locking unit 650 may include a locking bracket 652 and a locking arm 654.

The locking bracket 652 may be coaxial with the shaft 620, and may be coupled to the needle unit 630. The locking bracket 652 may be coupled to the connecting rod 634 of the needle unit 630 or the plunger 632 of the needle unit 630.

The locking arm 654 may be elastically supported by the locking bracket 652, and may be moved in a direction, in which the locking arm 654 becomes closer to or spaced apart from the shaft 620. The hook recess 622 or the hook 656 may be formed on an inner surface of the locking arm 654.

Hereinafter, it will be defined for convenience of description that the hook recess 622 is provided on an outer peripheral surface of the shaft 620 and the hook 656 is provided on an inner surface of the locking arm.

Although it will be described later, the locking arm 654 may become closer to or spaced apart from the shaft 620 while being moved along the guide 660. Here, when the locking arm 654 becomes closest to the shaft 620, the hook 656 of the locking arm 654 may be locked to the hook recess 622 of the shaft 620. Further, when the locking arm 654 have become spaced apart from the shaft 620, the hook 656 of the locking arm 654 may be unlocked from the hook recess 622 of the shaft 620. Then, the locking arm 654 may have an elastic force that faces the guide 660 to be spaced apart from the shaft 620.

In an embodiment, the locking arm 654 may have a shape of a cantilever that extends from the locking bracket 652 toward the shaft 620.

In an embodiment, a plurality of locking arms 654 may be provided, and the plurality of locking arms 654 may be disposed along a circumference of the locking bracket 652. In this case, the locking arms 654 may be firmly locked to the hook recesses 622 of the shaft 620 through the hook 656 of the plurality of locking arms 654.

In an embodiment, the locking arm 654 may include a first outer diameter unit 654*a*, a gradient unit 654*b*, and a second outer diameter unit 654*c*.

The first outer diameter unit 654*a* may protrude and extend from the locking bracket 652. The first outer diameter unit 654*a* has an outer diameter that is smaller than that of the second outer diameter unit 654*c*.

The gradient unit 654*b* may have a specific gradient corresponding to a gradient path unit 664 of the guide 660, which will be described later, and may protrude and extend from the first outer diameter unit 654*a*. As the gradient unit 654*b* has the specific gradient corresponding to the gradient path unit 664 of the guide 660, it may be easily moved along the gradient path unit 664 of the guide 660. A description thereof will be made later.

The second outer diameter unit 654*c* may be stepped from the first outer diameter unit 654*a*, may have an outer diameter that is larger than that of the first outer diameter unit 654*a*, and may protrude and extend from the gradient unit 654*b*.

The guide 660 is provided in the cylinder 610 to guide movement of the locking arm 654. Then, the guide 660 may have a tubular shape as a whole, and the locking unit 650 may be accommodated in an interior thereof. As described above, the locking arm 654 may be moved along an inner peripheral surface of the guide 660 as it has an elastic force that faces the guide 660, that is, an elastic force that faces a radial direction.

Meanwhile, a stopper 680 for restricting movement of the locking arm 654 may be provided between the shaft 620 and the locking arm 654. The stopper 680 may be coupled to an upper surface of the guide 660, and functions to restrict the locking arm 654 from being moved up to the top dead point or more. The stopper 680 may have a tubular shape, an interior of which is hollow, and the shaft 620 may pass through the interior thereof.

The guide 660 may include an unlocking path unit 662, the gradient path unit 664, and a locking path unit 666. Here, the unlocking path unit 662 may be provided in an area of the guide 660, which is adjacent to the shaft 620, the gradient path unit 664 may be provided between the unlocking path unit 662 and the locking path unit 666, and the locking path unit 666 may be provided on another area of the guide 660, which is adjacent to the needle unit 630.

In the unlocking path unit 662, the locking arm 654 may be moved while the locking arm 654 is spaced apart from the shaft 620 and the hook 656 of the locking arm 654 is unlocked from the hook recess 622 of the shaft 620. To this end, the unlocking path unit 662 may be stepped from the locking path unit 666, and may have an inner diameter that is larger than that of the locking path unit 666.

In the gradient path unit 664, the locking arm 654 may become closer to or spaced apart from the shaft 620 according to a movement direction of the locking arm 654. To this end, the gradient path unit 664 may have a specific gradient between the unlocking path unit 662 and the locking path unit 666, and in detail, the gradient path unit 664 may have an inner diameter of which decreases as it goes from the unlocking path unit 662 to the locking path unit 666.

Accordingly, when the locking arm 654 is moved in a direction that faces the locking path unit 666 from the gradient path unit 664, the gradient path unit 664 guides the locking arm 654 in a direction, in which the locking arm 654 becomes closer to the shaft 620. As a result, when the locking arm 654 becomes closest to the shaft 620, the hook 656 of the locking arm 654 may be locked to the hook recess 622 of the shaft 620.

Furthermore, when the locking arm 654 is moved in a direction that faces the unlocking path unit 662 from the gradient path unit 664, the gradient path unit 664 guides the locking arm 654 in a direction, in which the locking arm 654 becomes spaced apart from the outer peripheral surface of the shaft 620. As a result, after the locking arm 654 is spaced apart from the shaft 620, the hook 656 of the locking arm 654 may be unlocked from the hook recess 622 of the shaft 620. Then, a distal end of the shaft 620 may push the locking arm 654 in a direction, in which the locking arm 654 is spaced apart from the shaft 620.

In the locking path unit 666, the locking arm 654 may be moved while the locking arm 654 is adhered to the shaft 620 and the hook 656 of the locking arm 654 is locked to the hook recess 622 of the shaft 620. To this end, the unlocking path unit 662 may be stepped from the locking path unit 666, and may have an inner diameter that is smaller than that of the locking path unit 666.

Hereinafter, an operation of the locking unit 650 of the medicine injection tip 600 according to an embodiment of the inventive concept will be described.

FIGS. 5 to 10 are cross-sectional views illustrating operation states of a locking unit of a medicine injection tip according to an embodiment of the inventive concept, based on the cross-sectional view of FIG. 4.

First, as illustrated in FIG. 4, the shaft 620 may be disposed at a location that is spaced apart from the locking unit 650 at a specific interval in an initial stage.

Figure 5:
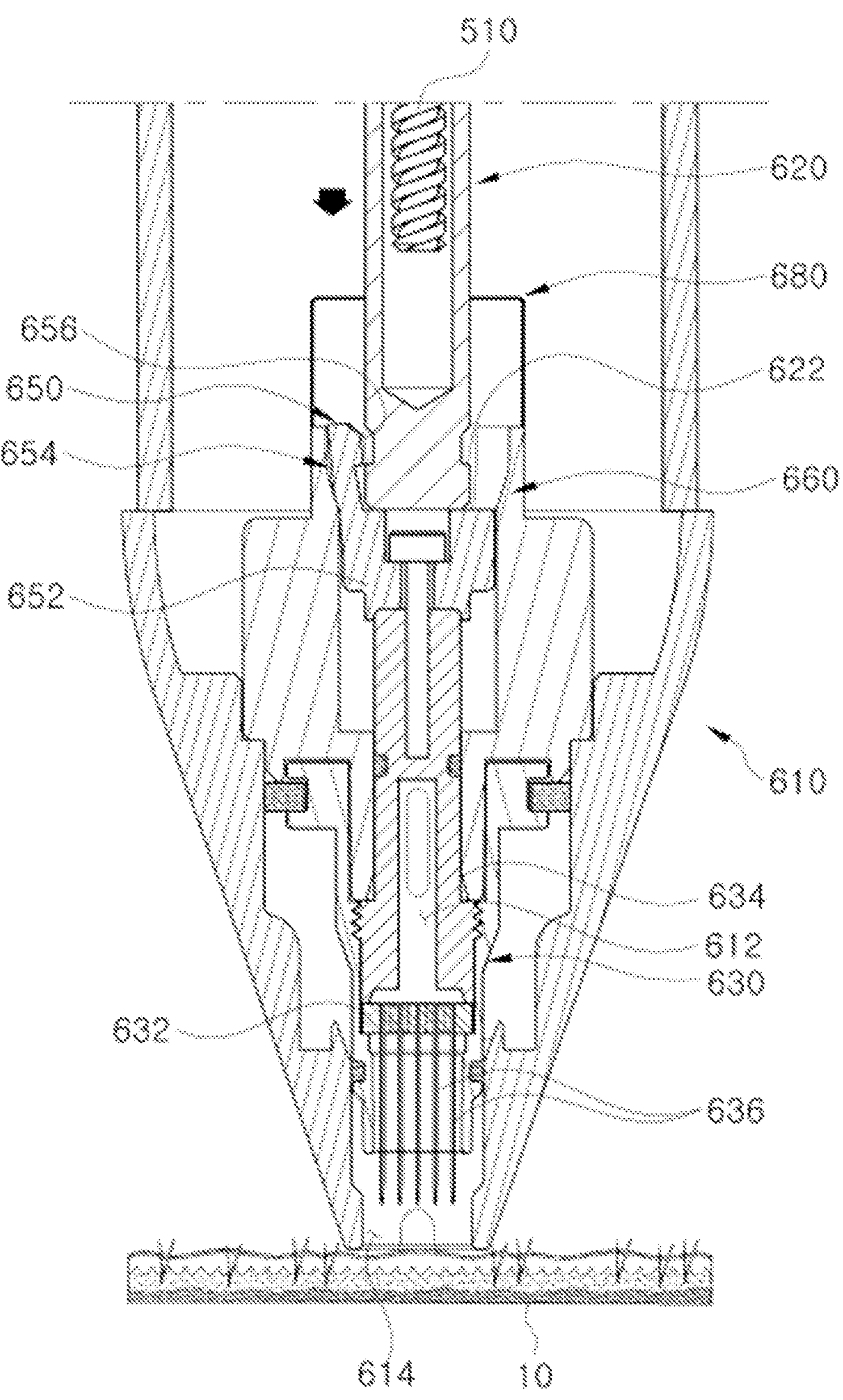
FIGS. 5 to 10 are cross-sectional views illustrating operation states of a locking unit of a medicine injection tip according to an embodiment of the inventive concept, based on the cross-sectional view of FIG. 4.

Next, as illustrated in FIG. 5, when the shaft 620 is moved in a direction, in which the shaft 620 becomes closer to the skin 10, the distal end of the shaft 620 is inserted into the locking unit 650.

Next, when the shaft 620 is further moved in a direction, in which the shaft 620 becomes closer to the skin 10, the shaft 620 pushes the locking unit 650 and the needle unit 630 in a direction, in which they become closer to the skin 10. Then, because the locking arm 654 of the locking unit 650 is moved along the unlocking path unit 662 of the guide 660, the locking arm 654 is moved while being spaced apart from the shaft 620. As a result, the shaft 620 is moved in a direction, in which the shaft 620 becomes closer to the skin 10 while pushing the locking unit 650. At the same time, the needle unit 630 is moved in a direction, in which the needle unit 630 becomes closer to the skin 10.

Figure 6:
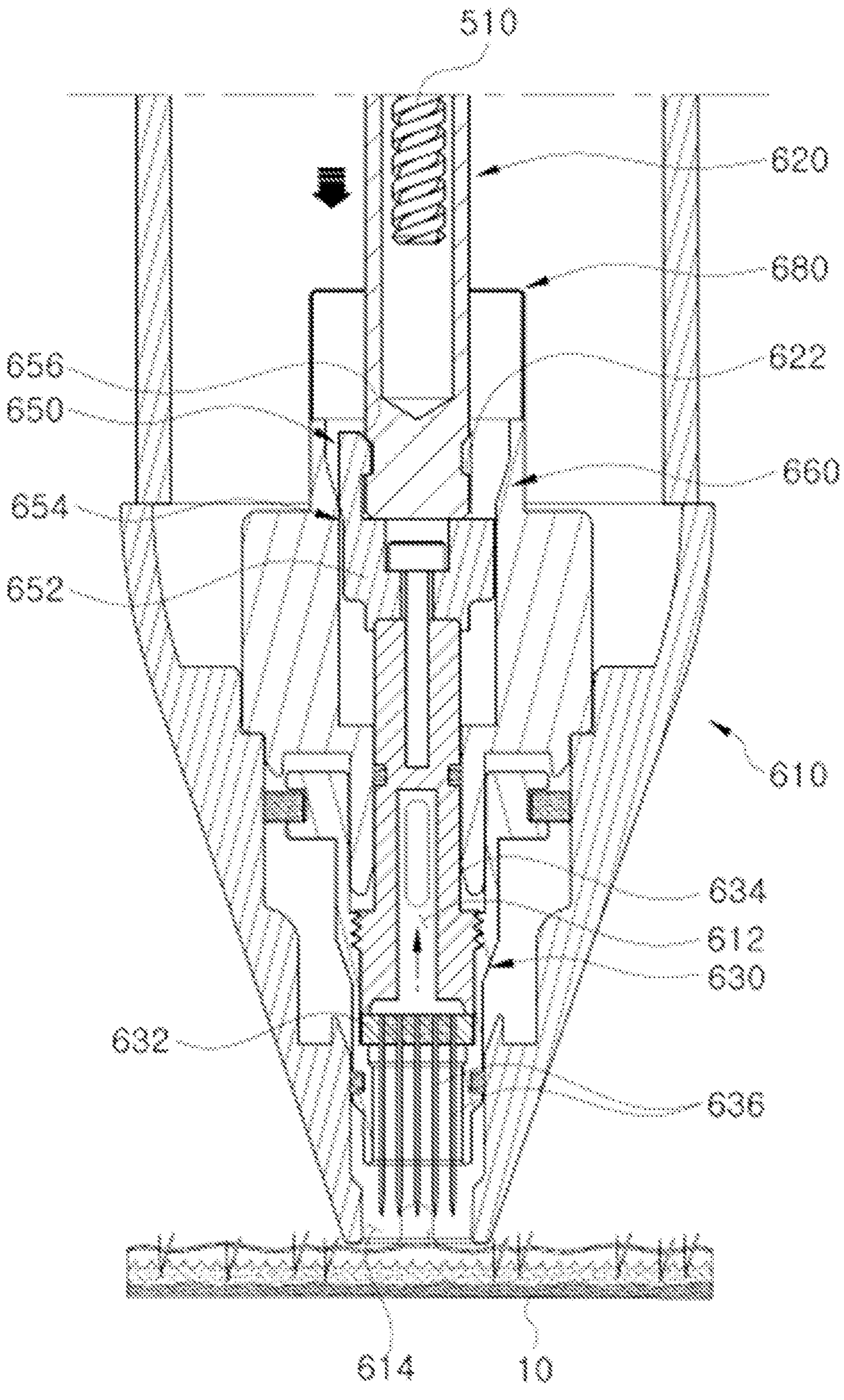

Next, as illustrated in FIG. 6, when the shaft 620 is further moved in a direction, in which the shaft 620 becomes closer to the skin 10, the shaft 620 additionally pushes the locking unit 650 and the needle unit 630 in a direction, in which they become closer to the skin 10. Then, because the locking arm 654 of the locking unit 650 is moved along the gradient path unit 664 of the guide 660, the locking arm 654 is moved in a direction, in which the locking arm 654 becomes closer toward the shaft 620. Thereafter, the hook 656 of the locking arm 654 is locked to the hook recess 622 of the shaft 620. At the same time, the needle unit 630 is moved in a direction, in which the needle unit 630 becomes closer to the skin 10.

Meanwhile, when the locking arm 654 is moved along the gradient path unit 664 of the guide 660, the gradient unit 654*b* of the locking arm 654 may be easily moved along the gradient path unit 664 of the guide 660.

Figure 7:
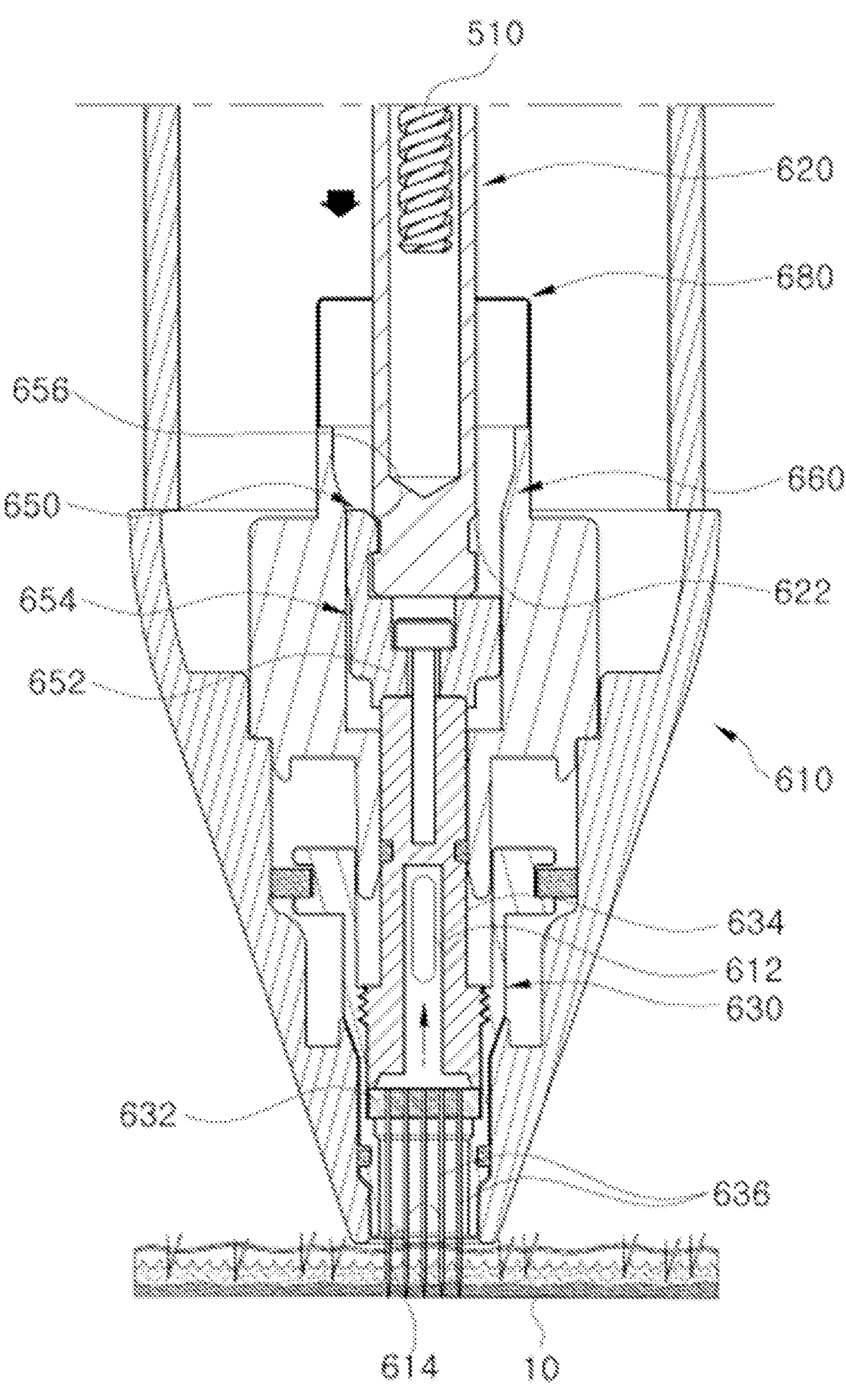

Next, as illustrated in FIG. 7, when the shaft 620 is further moved in a direction, in which the shaft 620 becomes closer to the skin 10, the shaft 620 additionally pushes the locking unit 650 and the needle unit 630 in a direction, in which they become closer to the skin 10. Then, because the locking arm 654 of the locking unit 650 is moved along the locking path unit 666 of the guide 660, the locking arm 654 is moved while being adhered to the shaft 620. As a result, the hook 656 of the locking arm 654 is moved while being locked to the hook recess 622 of the shaft 620. At the same time, after being moved in a direction, in which the needle unit 630 becomes closer to the skin 10, the needle unit 630 is inserted into the skin 10 in contact with the cylinder 610.

Figure 8:
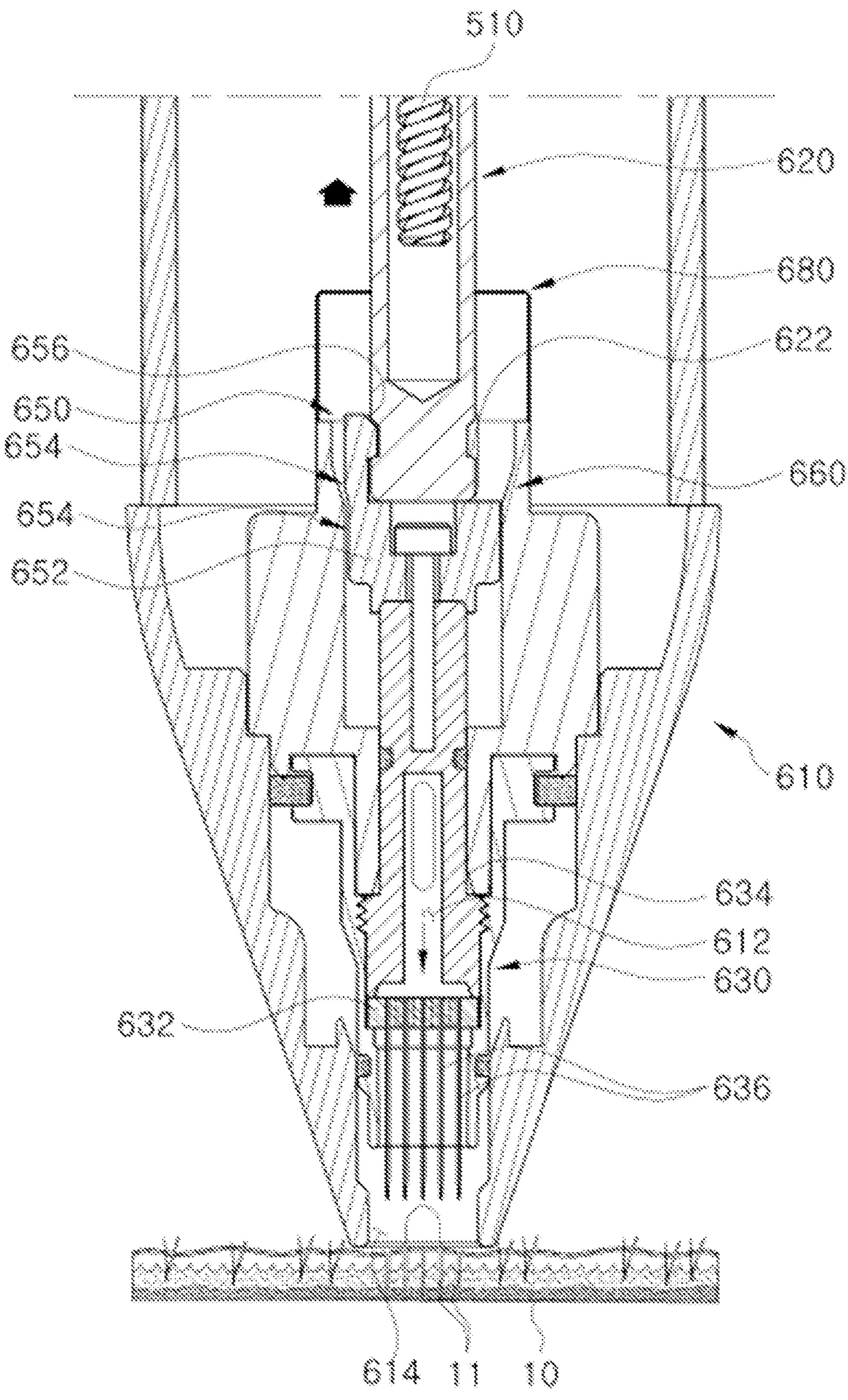

Next, as illustrated in FIG. 8, because the shaft 620 and the needle unit 630 are locked to each other by the locking unit 650 when the shaft 620 is moved in a direction, in which the shaft 620 is spaced apart from the skin 10, the locking unit 650 and the needle unit 630 are moved in a direction, in which they are spaced apart from the skin 10 as the shaft 620 is moved. Then, because the locking arm 654 of the locking unit 650 is moved along the locking path unit 666 of the guide 660, the locking arm 654 is moved while being adhered to the shaft 620. As a result, the hook 656 of the locking arm 654 is moved while being locked to the hook recess 622 of the shaft 620. At the same time, the needle unit 630 is discharged from the skin 10 after being moved in a direction, in which the needle unit 630 is spaced apart from the skin 10.

Figure 9:
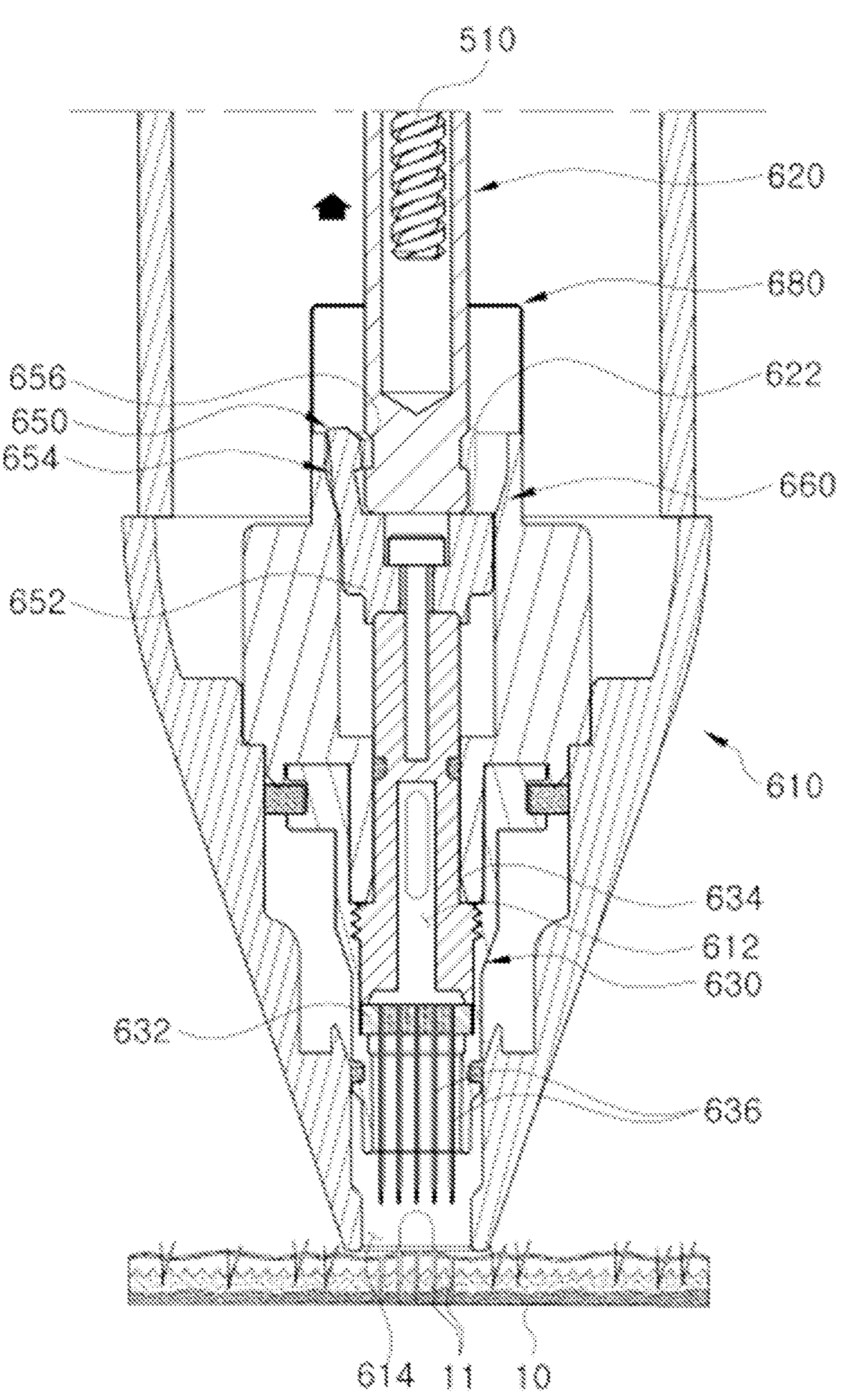

Next, as illustrated in FIG. 9, because the shaft 620 and the needle unit 630 are locked to each other by the locking unit 650 when the shaft 620 is further moved in a direction, in which the shaft 620 is spaced apart from the skin 10, the locking unit 650 and the needle unit 630 are moved in a direction, in which they are spaced apart from the skin 10 as the shaft 620 is moved. Then, because the locking arm 654 of the locking unit 650 is moved along the gradient path unit 664 of the guide 660, the locking arm 654 is moved in a direction, in which the locking arm 654 is gradually spaced apart from the shaft 620. Thereafter, the hook 656 of the locking arm 654 is unlocked from the hook recess 622 of the shaft 620. At the same time, the needle unit 630 is moved in a direction, in which the needle unit 630 is spaced apart from the skin 10, and returns to the initial location.

Figure 10:
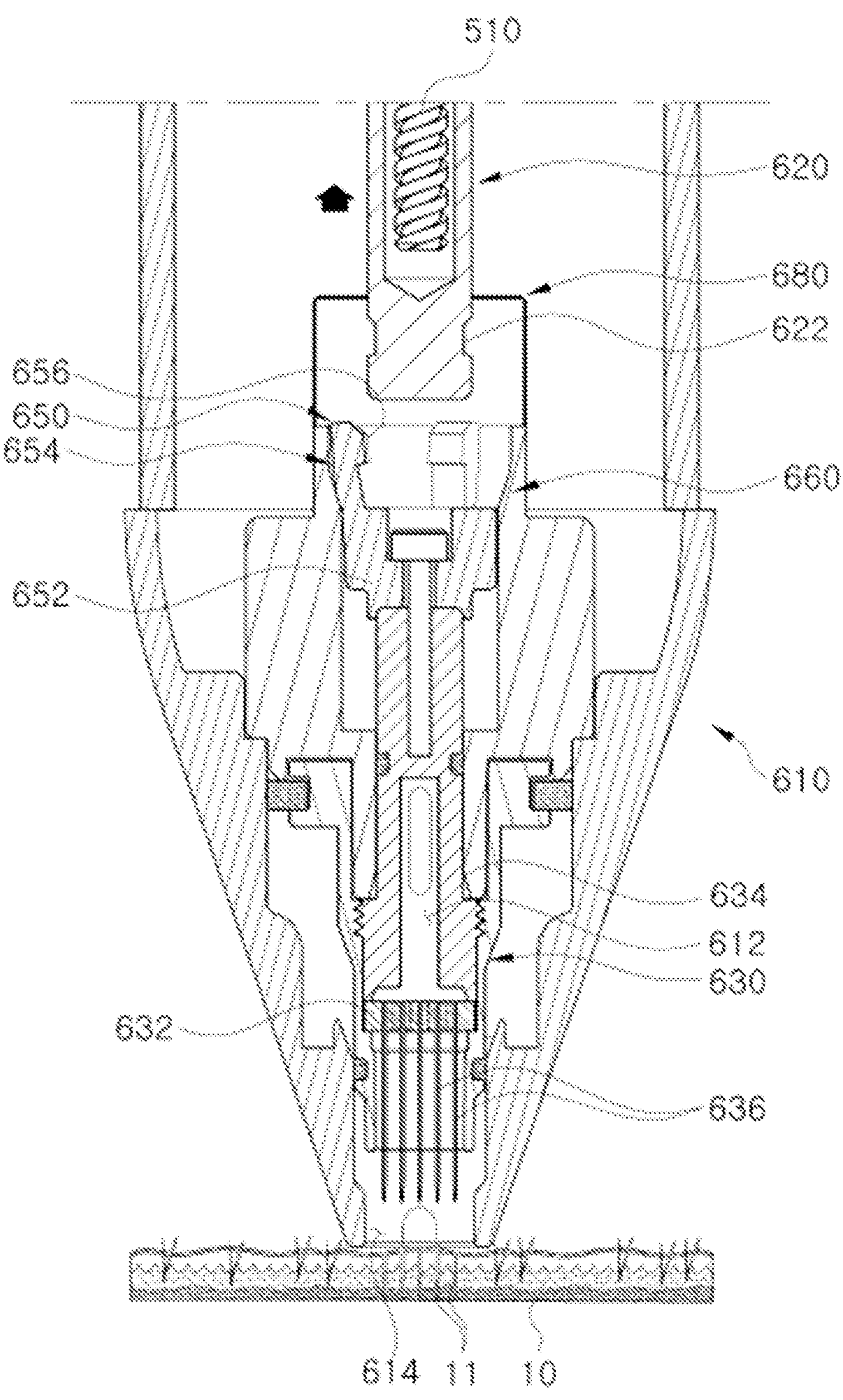

Next, as illustrated in FIG. 10, because the locking of the shaft 620 and the needle unit 630 by the locking unit 650 is released when the shaft 620 is further moved in a direction, in which the shaft 620 is spaced apart from the skin 10, only the shaft 620 is moved in a direction, in which the shaft 620 is spaced apart from the skin 10 and returns to the initial location.

Accordingly, as the needle 636 of the inventive concept is inserted into and discharged from the skin 10 due to the movement of the shaft 620, the needle 636 may be smoothly inserted into and discharged from the skin 10.

The medicine injection tip 600 according to an embodiment of the inventive concept may further include a medicine supply unit (not illustrated).

The medicine supply unit (not illustrated) may include a medicine supply passage (not illustrated) that is provided in the cylinder 610 and supplies the medicine to a vicinity of the skin 10 when a negative pressure is formed in the vicinity of the skin 10, into which the needle 636 is inserted. As will be described later, the medicine supply passage (not illustrated) may be formed in an interior of a medicine nozzle (nozzle).

The medicine supply unit (not illustrated) may include a medicine storage unit (not illustrated) and the medicine nozzle (not illustrated).

The medicine storage unit may be accommodated in the cylinder 610 and store medicine to be supplied to the medicine supply passage (not illustrated). For example, a medicine container, in which the medicine may be stored, may be used as the medicine storage unit (not illustrated).

The medicine nozzle (not illustrated) connects the medicine storage unit (not illustrated) and a distal end of the cylinder 610. The medicine supply passage (not illustrated) may be formed in an interior of the medicine nozzle (not illustrated). Furthermore, a check valve (not illustrated) for delivering the medicine from the medicine storage unit (not illustrated) only to the distal end of the cylinder 610 may be provided in the medicine supply passage (not illustrated).

As set forth above, according to the medicine injection tip, the hand piece, and the skin treatment device according to the embodiment of the inventive concept, the needle may be smoothly inserted into and discharged from the skin as the needle is inserted into and discharged from the skin due to the movement of the shaft.

The effects of the inventive concept are not limited thereto, and other unmentioned effects of the inventive concept may be clearly appreciated by those skilled in the art as set forth above.

Hereinbefore, although the exemplary embodiments of the inventive concept have been described with reference to the accompanying drawings, it will be understood by those skilled in the art to which the inventive concept pertains that the inventive concept can be carried out in other detailed forms without changing the technical spirits and essential features thereof. Therefore, the above-described embodiments are exemplary in all aspects, and should be construed not to be restrictive.

DESCRIPTION OF REFERENCE NUMERALS

10: SKIN
11: INVASION HOLE
100: BODY
200: DISPLAY MODULE
300: MANIPULATION MODULE
400: CABLE
500: HAND PIECE
510: SCREW SHAFT
600: MEDICINE INJECTION TIP
610: CYLINDER
612: FIRST SPACE
614: SECOND SPACE
620: SHAFT
622: HOOK RECESS
630: NEEDLE UNIT
632: PLUNGER
632A: CHANNEL
634: CONNECTING ROD
636: NEEDLE
650: LOCKING UNIT
652: LOCKING BRACKET
654: LOCKING ARM
654A: FIRST OUTER DIAMETER UNIT
654B: GRADIENT UNIT
654C: SECOND OUTER DIAMETER UNIT
656: HOOK
660: GUIDE
662: UNLOCKING PATH UNIT
664: GRADIENT PATH UNIT
666: LOCKING PATH UNIT
680: STOPPER

What is claimed is:

1. A medicine injection tip comprising:

a cylinder;

a shaft provided in the cylinder and movable in a direction toward or away from skin;

a needle unit disposed between the shaft and the skin;

a locking unit provided between the shaft and the needle unit and configured to lock or unlock the shaft as the shaft is moved, wherein a hook recess is provided in any one of the shaft or the locking unit, and wherein a hook operable to be locked to or unlocked from the hook recess is provided in the other of the shaft or the locking unit, and the hook unlocks from the hook recess to unlock the shaft in response to the shaft moving away from the skin; and a driving module configured to move the shaft, wherein:

moving the shaft toward the skin causes (1*a*) the hook to be locked to the hook recess at a top region of the locking unit, and (1*b*) the shaft to be moved to a bottom region of the locking unit when locked, and moving the shaft away from the skin causes (2*a*) the hook to be unlocked from the hook recess at the top region of the locking unit, and (2*b*) the shaft to be moved to an initial position when unlocked.

2. The medicine injection tip of claim 1, wherein the locking unit comprises:

a locking bracket being coaxial with the shaft and connected to the needle unit; and a locking arm elastically supported by the locking bracket and being moved in a direction, in which the locking arm becomes closer to or spaced apart from the shaft, wherein the hook recess or the hook is formed in the locking arm.

3. The medicine injection tip of claim 2, further comprising:

a guide provided in the cylinder and configured to guide movement of the locking arm.

4. The medicine injection tip of claim 3, wherein the guide comprises:

an unlocking path unit configured such that the locking arm is moved while being spaced apart from the shaft and while the hook recess and the hook are unlocked from each other; and a locking path unit configured such that the locking arm is moved while being adhered to the shaft and while the hook recess and the hook are locked to each other.

5. The medicine injection tip of claim 4, wherein the unlocking path unit is stepped from the locking path unit and has an inner diameter that is relatively larger than that of the locking path unit.

6. The medicine injection tip of claim 4, wherein the guide comprises a gradient path unit having a specific gradient between the unlocking path unit and the locking path unit.

7. The medicine injection tip of claim 6, wherein the locking arm further comprises:

a first outer diameter unit protruding and extending from the locking bracket;

a gradient unit having a specific gradient corresponding to the gradient path unit and protruding and extending from the first outer diameter unit; and a second outer diameter unit stepped from the first outer diameter unit, having an outer diameter that is larger than that of the first outer diameter unit, and protruding and extending from the gradient unit.

8. The medicine injection tip of claim 1, wherein the cylinder is configured to supply a medicine to a vicinity of the skin when a negative pressure is formed at the vicinity of the skin, into which a needle is inserted.

9. The medicine injection tip of claim 8, wherein the needle unit comprises:

a plunger forming a first space and a second space in an interior of the cylinder; and the needle disposed in the first space and fixed to the plunger, wherein the plunger comprises a channel connecting the first space and the second space.

10. The medicine injection tip of claim 9, wherein the needle forms an invasion hole in the skin through which the needle is inserted into and discharged from the skin as the needle unit moves, wherein inserting the needle into the skin forms a negative pressure in the second space that suctions the medicine, and wherein discharging the needle from the skin forms a positive pressure in the second space that injects the medicine into the invasion hole in the skin.

11. The medicine injection tip of claim 9, wherein electric energy is applied to the needle.

12. The medicine injection tip of claim 9, wherein electric energy applied to the needle generates thermal energy in the skin.

13. A hand piece, on which the medicine injection tip of claim 1 is mounted.

14. A skin treatment device comprising:

the medicine injection tip of claim 1; and a hand piece, on which the medicine injection tip is mounted.

15. A medicine injection tip comprising:

a cylinder;

a shaft positioned in the cylinder and movable in a first direction toward an extended position and a second direction toward a retracted position;

a needle unit;

a locking unit positioned between the shaft and the needle unit and operable to lock or unlock the needle unit and the shaft, the locking unit and the shaft defining a coupling including a hook recess and a hook provided on one or the other of the shaft or the locking unit, respectively, such that the hook unlocks from the hook recess to unlock the shaft in response to the shaft moving in the second direction toward the retracted position; and a driving module configured to move the shaft in the first and second directions, wherein moving the shaft in the first direction causes the hook to be locked to the hook recess at a top region of the locking unit and the shaft to be moved to a bottom region of the locking unit, and moving the shaft in the second direction causes the hook to be unlocked from the hook recess at the top region of the locking unit and the shaft to be moved to an initial position.

* * * * *